(12) United States Patent
Fernandez

(10) Patent No.: US 6,203,563 B1
(45) Date of Patent: Mar. 20, 2001

(54) HEALING DEVICE APPLIED TO PERSISTENT WOUNDS, FISTULAS, PANCREATITIS, VARICOSE ULCERS, AND OTHER MEDICAL OR VETERINARY PATHOLOGIES OF A PATIENT

(76) Inventor: Ernesto Ramos Fernandez, Artigas 1087 1 flr, A, Buenos Aires (AR)

( * ) Notice: Subject to any disclaimer, the term of this patent is extended or adjusted under 35 U.S.C. 154(b) by 0 days.

(21) Appl. No.: 09/320,043

(22) Filed: May 26, 1999

(51) Int. Cl.⁷ .................................................. A61B 17/08
(52) U.S. Cl. ............................................................ 606/215
(58) Field of Search ................................... 606/213, 214, 606/215, 216; 128/897

(56) References Cited
U.S. PATENT DOCUMENTS 5,636,643 * 6/1997 Argenta et al. ......................... 602/42

* cited by examiner

Primary Examiner—Michael H. Thaler
Assistant Examiner—Vy Q. Bui
(74) Attorney, Agent, or Firm—Alfred M. Walker

(57) ABSTRACT

A healing device applied to wounds, fistulas, pancreatitis, varicose ulcers, and other medical or veterinary pathologies includes a compacting chamber for covering the wound over the affected or diseased zone of the patient. The compacting chamber is defined by a self adhesive polymeric material laminar sheet, made out of a waterproof material. The compacting chamber has a replaceable mass of aerated polymer fiber flock therewithin, as a wound-stabilizing dressing. The compacting chamber uses a vacuum for deforming and compacting a mass of polymer fiber flock into effective healing contact with the wound. The vacuum means is terminated upon achieving compaction of the mass of polymer fiber flock and upon effective healing contact of the mass of polymer fiber flock with the wound.

9 Claims, 4 Drawing Sheets

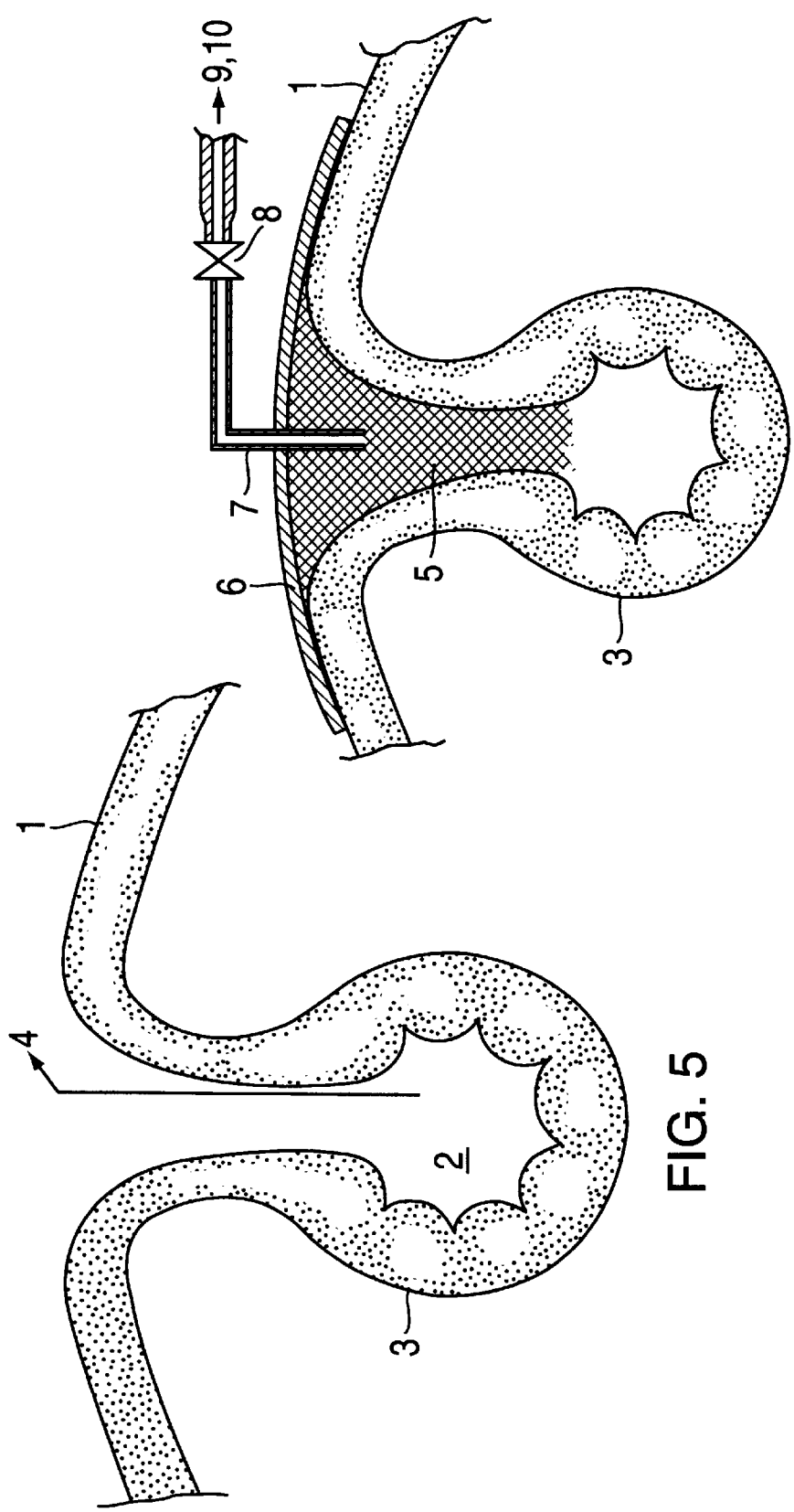

HEALING DEVICE APPLIED TO PERSISTENT WOUNDS, FISTULAS, PANCREATITIS, VARICOSE ULCERS, AND OTHER MEDICAL OR VETERINARY PATHOLOGIES OF A PATIENT

The main object for this invention is a healing device applied to wounds, fistulas, pancreatis, varicose ulcers and other medical or veterinary pathologies requiring compacting into said wound an aerated material by means of atmospheric depression, and it has as its secondary object the method for applying said device.

BACKGROUND AND PRIOR ART OF THIS INVENTION

It is well know to professionals skilled in the art of healing, that a wound at any part of the human body can be provoked either by a pathological agent, as well through a traumatic agent. In either cases, the final result is a wound which segregates fluids, accumulates detritus and creates a bacteria breeding site, which in direct function of the nature and size of the wound, may impede its healing. On the other hand, a fistula is an orifice open from within an organ or limb in the human body, with an outlet.

A healing process implies cleansing the wound, drying same of noxious fluids, and since a wound may be considered as an infectious cavity within the body, a fistula is a wound defining a passage or opening communicating one of more internal organs with the outer environment. The healing process for these medical pathologies are successful when the wound is clean and dry, ceasing in its emission of humorous fluids and detritus. Most of these are provoked by the activity of bacteria and pathogenic agents, which according to their nature must have a sufficient threshold of oxygen pressure in order to live and multiply, or in the case of gangrene, the absence of oxygen is required for same to infest the body.

The necessary oxygen pressure for these bacteria, or the like, to thrive is attained at sea level at atmospheric pressure (760 mm Hg.), and in the case of gangrenes it has been found that a reasonable acceptable means of oxygenating the base of the gangrenous wound is to induce an increase of blood irrigation in its area. As a rule an infected wound produces an interface between the external environment and the base of the wound. It is also known that atmospheric air at a pressure of 760 mm Hg. has an average of 20% in oxygen. This means the oxygen present in air is responsible for 150 mm Hg. as measured in the pressure column. It is further common knowledge that any living organism needs an average column of 100 mm Hg. in oxygen in order to allow the oxygen exchange through its cell membrane, while under this oxygen pressure it is not possible to sustain life due to lack of the vital oxygen exchange.

In the following exposition, it will be only be made mention to a fistula in the abdominal region, which has interested a portion of intestine, short-circuiting the digestive tract, without this sole mention being capable to construe any limitation to the actual scope of this instant invention, which can be applied to any wound as above said, and specifically to fistulas in any part of the body, being this scope delimited by the first claim of this patent.

As known to the skilled in the art, a fistula implies some serious inconveniences, such as:

undernourishment, if said fistula is an intestinal fistula, with an elevated flow of humorous fluids;

loss of body fluids and electrolytes (such as blood, etc.)

a degradation process of the tissue in the area surrounding said fistula, since the body humours exiting from said wound acts as a ferment.

This means a fistula acts, like a true communication opening through which, (as in this chosen non limiting example) one or more portions of intestine are thus in direct communication with the external environment, short-circuiting the lower digestive tract.

Considering always the abdominal fistulas, it is believed post-chirurgic entero-cutaneous fistulas appears between 0.5 to 2% of all patients with abdominal operations. Depending on the treated pathology, and also considering if we are dealing with emergency surgery or programmed interventions, when and if a fistula papers, it aggravates the prognosis for the patient. The flow rate of the intestinal contents, its proteolitic activity, its anatomical placing, the peritoneal infection, the difficulty in the distal transit and the base illness, are causes whose combination averages a mortality rate between 20 to 40% of all patients thus affected.

Professionals skilled in the art knows that when a fistulae appears, they have two choices:

medical treatment, or chirurgic treatment.

As a rule, considering the inherent complications attached to a chirurgic treatment of fistulas, there is a tendency to try to obtain its obturation through medical treatment.

Chirurgy is not always practicable since the orifices segregates a high flow rate of intestinal liquids (an average of 1500 cc/ day), and the aggression of these liquids at its full final digestive process literally "digests" or "eats" the new tissue intended to precisely close the orifice. There exists an important relative pressure within the intestine, which pumps the liquids in a natural way towards the end of the digestive tract, helping same to exit with any contention through said fistula. In the operated cases the recidivate reaches around 20%.

Of the several procedures tried out in the past for the closing of fistula openings, no one gave the expected mortality reductions rate results.

Beginning by surgery, it has been already explained why same cannot prosper. It is known to have been tried to obturate the orifices with adhesives, including instant adhesivation, but it was not possible to maintain dry the wound area.

In order to reduce a secretion rate, traditionally it has been used a continues aspiration, applied to the wound, along with the prescription of antiexocrine medication, and this forces the patient to lay in bed, tending to create the necessary conditions for a pulmonary emboli, pulmonary hipostasia with risks of pulmonary infection.

It is also necessary to replace intravenously into the patient the lost electrolytes due to the secretion flow rate, and a long term parental feeding which produces a high mortality rate of due to these causes.

The last consideration given to fistulas treated with the known traditional methods is time: in effect, it has been known cases in which the patent has been subjected to post-surgery terms of several months, sometimes even almost an year, with being able to walk, and acute nutritional problems.

OBJECTS OF THIS INVENTION

It is a main object of this invention a device which allows at the same time to dry the wound, or fistula, or the excreted fluids, humors and detritus, while at the same time is capable of denying the necessary oxygen pressure at the interface (wound surface/ secreted fluid), and lastly, it allows the blood irrigation increase at the base of said interface, oxygenating same while it avoids the humidity from the secretions, which is the determinant factor of the bacterial growth. To this end it is important to remember that the secretions are a bacterial growing broth.

It is a further main object of this invention a device for treating wounds, fistulas, pancreatitis, varicose ulcers and other medical or veterinarian pathologies requiring atmospheric depression, compacting an aerated material in direct contact with said wound or fistula, stopping the secretion of fluid from the body to the exterior environment, and establishing the conditions allowing the patient to regenerate its own tissues, with the given time, closing the opening of the wound of fistula.

It is another object of this invention a device, which in the specific case of fistulas, allows to stop the drainage of internal fluids proper of the affected organ (such as the intestine) thus detaining its dysfunction, such as for example an aggravated undernourishment, or grave hemorrhage, such as in the case of varicose wounds.

It is a further object of the invention a device capable of creating a vacuum chamber (negative pressure) capable of compacting the aerated fibrous material, against the portion of the body against which this chamber is applied, determining a malleable structure of selective rigidity particularly apt for treating bone fractures in the members, etc.

It is an additional object of this invention a device which allows the patient to move within a determined environment and margin, even with its pathology under treatment (either a fracture, wound, fistula, etc.) avoiding additional injuries and/or complications due to a long postulation, such as lung embolism, pneumonia, malnutrition, atrophy, etc.

It is a secondary object of this invention the method through which this device can be used.

SUMMARY OF THIS INVENTION

The device of this instant invention consists in forming a compacting chamber over the affected or diseased zone of the patient, being this chamber defined by a self adhesive polymeric material laminar sheet, made out of a waterproof, with low deformation, two-axis oriented polymer, which adheres over at least a perimetral portion around the zone affected with the pathology to be treated; under said laminar sheet and in intimate contact with said pathology, it is placed a mass of polymer lox, made out of fibers with a diameter ranging from 0.0005 mm to 1 mm, and a length ranging from 3 cm up to 50 cm, being these fibers preferably chosen from crimped fibers placed with its axis substantially parallel the one to the other, or from a non-woven mass of flock, or from a fabric or web made out of said fibers with a web measure of 0.5 to 6 deniers; this laminar sheet is perforated by the end of an aspiration tube with is introduced into said mass of fibers, establishing an airtight relationship between said tube and said laminar sheet at said perforation; the outer end of said aspiration tube is connected to a flow valve, which at its turn connects to upper end of a vessel with a capacity ranging from 5 to 30 litters; said vessel is hermetically closed, and from its lower end it has a second flow valve, normally closed, determining a selective draining means for said vessel; this vessel defines a liquid, secretions, detritus and air collector from said area with said pathology, and from said vessel it is derived a vacuum meter calibrated between a maximum and minimum pressure, being this vacuum meter cooperative between these two pressure values with a shut-off valve the conduit which connects said vessel with said vacuum pump, thus determining the compactness of the polymeric flock reducing its volume and driving in its free ends against the walls of the patients afflicted zone providing a multiple anchoring and a mass of flock with a variable and adjustable amount of air therein enclosed, with a rigidity in direct function of the vacuum thus established in said chamber.

The secondary object of this invention is related to the steps through which this device can be used: this sequence of steps includes:

placing, over the zone of the patient afflicted with the pathology (for instance the orifice of the fistula and in all the volume of the wound thus delimited), a mass of polymeric flock , preferably of crimped fibers with a diameter from 0.0005 mm to 1 mm, and with a length in between 3 cms up to 50 cms, forming these fibers a bundle or a non-woven of flock, or a web with a web value of 05, to 6 deniers, forming an obturation plug in said fistula or a rigid layer against the bone fracture, and substantially at a level with the skin of the patient;

then placing over the zone with the pathology to be treated, and covering entirely same, a self adhesive polymeric material laminar sheet, made out of a low deformability, waterproof, two-axis oriented polyolefinic polymer, with a thickness between 10 to 30 microns, being this laminar sheet adhered against the skin of the patient by means of a known adhesive; creating a compacting airtight chamber over said area with the pathology to be treated, covering the skin of the patient over said area and covering said mass of flock as well, this laminar sheet can be of the self-adhesive kind;

this laminar sheet is perforated by the end of an aspiration tube with is introduced into said mass of fibers, establishing an airtight relationship between said tube and said laminar sheet at said perforation;

closing said first flow valve and producing the vacuum by activating the vacuum pump extracting the air contained within said chamber, sending same into said vessel, maintaining the activity of the vacuum pump until a negative pressure around −700 mmHg is attained, and with an air extraction flow rate of 100 to 300 litters/minute; once the programmed depression is attained, the vacuum pump is detained, either cutting of its power source or acting over the second flow valve or a shut-off valve;

keeping a stabilized depression in the vessel, the first flow valve is opened, producing the instant compactness of the mass of fibers;

a stabilized depression is maintained at reasonable constant values between said compacting chamber and said vessel, with the vacuum pump shut off, while said compactness of the mass of fibers is maintained at a value between 80 to 95% of the original value, forming a compacted mass due to the action of the vacuum, and a positive pressure over the abdominal walls compensating the pressures within the body of the patient;

at the necessary intervals of time, the first flow valve is closed, keeping the values of the vacuum in the airtight chamber, and opening the second flow valve producing the draining of the vessel's contents, then closing said second flow valve and opening one more the first flow valve;

repeat these operations all the necessary time required until the healing process has been completed.

In order to provide a working example of a construction for the above said invention, the following drawings are enclosed, along with the following explanation of said one construction, given for the sole purpose of proving an explanation as to one of the ways this invention can be construed, without providing these drawings and said explanation a limitation to the scope of the invention, which is determined by the claims in the corresponding claims chapter.

FIG. 2 shows one of the possible ways to apply this device for treating bone fractures, or the like;

FIG. 5 shows an abdominal open fistula;

FIG. 6 shows the fistula of FIG. 5, with the device according to this instant invention, partially illustrated, applied over same;

Figure 1:
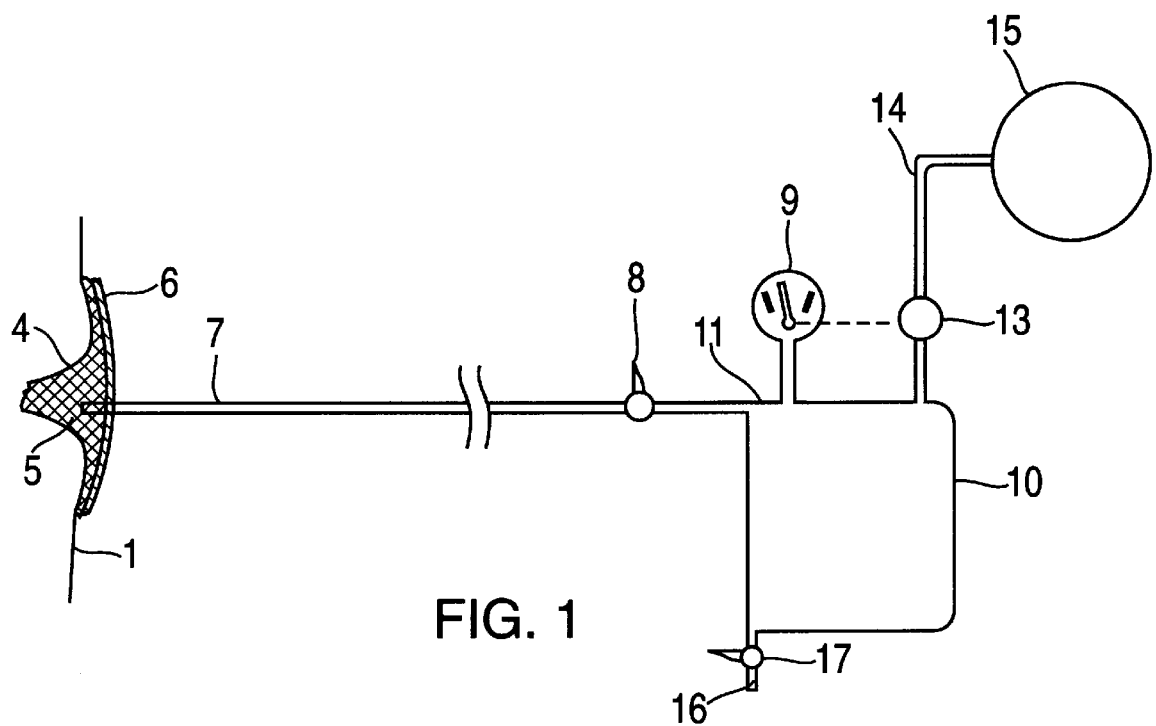
FIG. 1 shows the layout of the device according to this invention.

In FIG. 1 it is observed how, over a portion of skin (1) of a patient, it is placed a laminar sheet (6) according to the above given specifications, adhered to (1) by having at least a portion of same coated with a strong anti-allergic adhesive. This laminar sheet (6) covers the cavity of a generic wound (4), which has been previously filled with a bundle of the fibrous material (5) above indicated (flock).

Piercing said laminar sheet (6) we have the end of a conduit (7) which pierces said sheet with an air-tight relationship. Under laminar sheet (6) and with said mass (5) of flock it is created over the pathology to be treated, an airtight chamber filled with said flock. Conduit (7) is extended up to a first flow valve (8), which after this connects with the upper end of vessel (10). From said vessel (10) it is derived at (12) a vacuum meter (9) which may be connected to a flow valve (13). This flow valve preferably is a solenoid valve capable of shutting off conduit (14) which communicates vessel (10) with a vacuum pump (15)). From the bottom of vessel (10) a drainage conduit (16) with a second flow valve (17) is derived.

Figure 10:
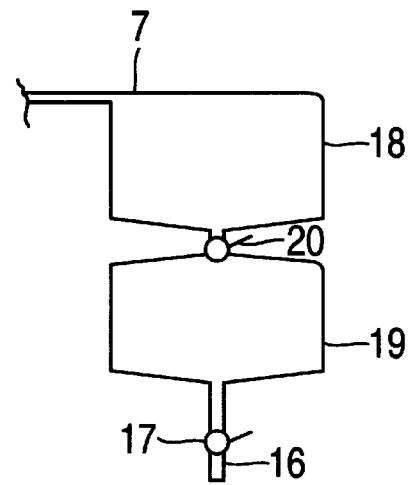
FIG. 10 shows another design for the accumulation vessel.

In another embodiment of this same invention (please see FIG. 10), the vessel (10) is divided into two vessels (18, 19), respectively an upper vessel and a lower vessel, joined by a conduit with a third flow valve (20). It is also possible this vessel (10) may be separated into two half-vessels by means of in inner wall, being both half-vessels communicated through said third flow valve (20).

These last embodiments, are suitable for a complete automatization of this device, acting on the vacuum meter which at its turn acts on the flow valve, obtaining an automatic operation governed through a microchip.

A third and last embodiment exists, in which after said first flow valve (8), conduit (7) is derived into an upper and a lower branch, not illustrated in the drawings, which allows a better drainage control of the fluids in said vessel, acting the lower branch as a fluid's trap.

When the first flow valve is opened with the vacuum pump (15) detained, it assures the liquids and detritus enters only into said vessel (10, 18, 19) when the compacting vacuum is produced, and not within said pump (15).

Figure 2:
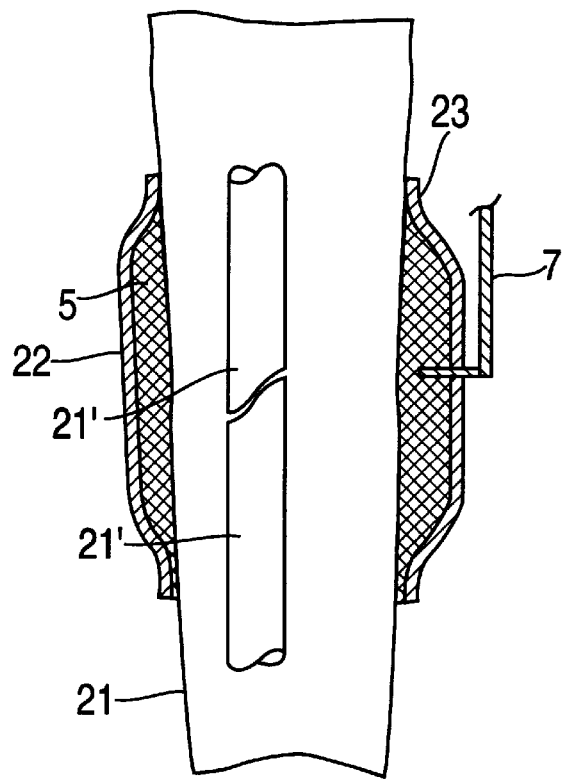
Figure 7:
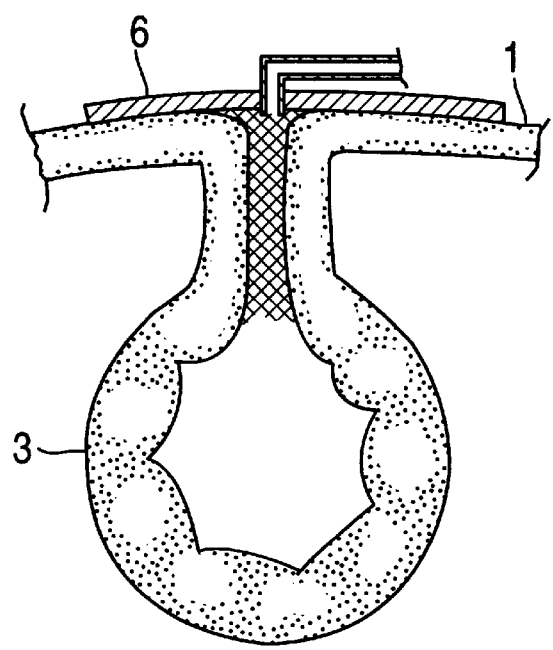
FIG. 7 shows schematically, the results of compacting.

In FIG. 2 it is observed another way to use this instant invention, which replaces the traditional plaster castings in the healing of bone fractures. In effect, it is indicated at (21) a member of the patient, being (21') its fractured bone.

On this member (21), around this fractured bone (21') it is placed an annular film (22), adhered to the skin through the film's border areas (23), thus defining an inner airtight chamber which is filled with said flock (5). Conduit (7) is then introduced into said chamber, and the compacting of the fibers is performed, establishing a semi-rigid mass surrounding the fractured zone, which rigidity is selectively controllable varying the vacuum extent, while retaining the necessary degree of flexibility.

Figure 3:
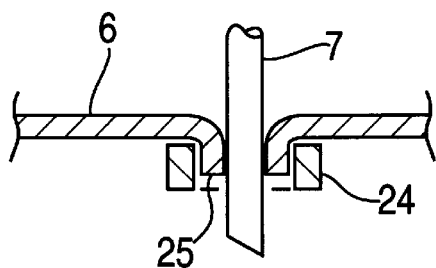
FIGS. 3 and 4 shows two different ways the aspiration tube can penetrate within the laminar sheet and airtight against this opening.
Figure 4:
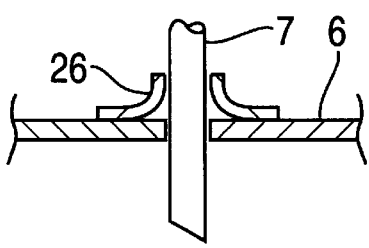

FIGS. 3 to 4 are showing two hermetically coupling means joining the film (6) and the aspiration conduit (7). One of the proposed embodiments (please see FIG. 3) which is obviously non exclusive nor restrictive to the scope of this instant invention, is to place a ring (24) adhered under film (6), which when penetrated by conduit (7) is deformed, creating the annular lips (25) between the inner perimeter (24) and said conduit (7) creating the conditions for an absolute airtight connection, with the possible aid of an external sealing filler.

At FIG. 4 it is observed another embodiment to this same end, consisting in placing over the film (6) an annular ring with an upwards directed annular flange (26), through which it is tightly passed said conduit (7), which penetrates the subjacent film (6).

Starting with the analysis of FIGS. 5 to 9, it is observed at FIGS. 5, 6 and 77 that reference (1) indicates a portion of the abdomen of the patient, which is suffering from a fistula (2) in communication with the intestine (3), and through this fistula the inner fluids (4) are given an outlet. Of course this diagram is a mere simplified illustration of the more complicated problems implied by suffering a fistula.

At FIG. 6 it is shown how said fistula (2) has been filled in with a mass of crimped fibers (5), preferably polyesters. As already said, this flock is made out from fibers with a diameter of 0.0005 mm up to 1 mm, and a length between 3 cms up to 50 cms, and preferably these fibers is made out in a bundle of fibers, or a non-woven blanket, with a mesh value between 0.5 to 6 deniers.

PERFORMING OF THIS DEVICE

The vacuum pump (15) is capable to reduce the pressure up top −700 Hgmm, with a 100–300 litters/min. flow rate.

Supposing the wound with the flock already placed into it, and covered by said polymeric laminar film (6), the film is perforated by the tube (7) establishing between said tube and film and air-tight relationship, connecting this tube (7) to the vacuum pump, with the flow-valve (8) in its closed position. Under these conditions, the air is pumped out from the wound, creating a depression up to −700 Hgmm. Once this vacuum has been created, the pump (15) is stopped, and the flow-valve (13) is closed, while the first flow-valve (8) is opened, creating a sudden and important suction, through (7) in said hermetic chamber, compacting the fibers and draining air and liquids through said fibers; these fibers are thus compacted and they are anchored against the walls of the wound (orifice), and against the skin of the patient and tissue of the wound, creating an hermetic plug and a blanket with a controlled and variable rigidity, while the polymeric film is inwardly flexed, against the zone with the pathology, pressing inwardly this mass of fibers (please see FIG. 7).

There are no limitations to the number of times this compacting operation can be performed, and it is possible to compact the fibers for a determined time, then uncompact, or to close valve (8) and unconnecting the tube (7), allowing the patient to walk, and inclusively it is possible to connect the patient with a portable vacuum source, which allows to maintain the seal and walk at the same time.

In the following statistical Table there are given values of the effective healing performed on a group off patients treated with this invention, during the experimental evaluation of this instant invention performed in the years 1985 up to 1991.

TABLE 1

Patients treated with fistula and results obtained

| Patient | Initials | Sex | Age | Diagnostic | Fistula | Results |
|---|---|---|---|---|---|---|
| 1 | AJ | M | 32 | Peritonitis | Cecal. | Healed |
| 2 | JF | M | 26 | Bullet wound | Yeyun. | Healed |
| 3 | NJ | M | 28 | Bullet wound | Heal. | Healed |
| 4 | VZ | M | 40 | Perforated ulcer | Duod. lateral | Healed |
| 5 | ML | M | 52 | Peritonitis | Yeyun. | Healed |
| 6 | MF | F | 65 | Fecal Periton. | Duod. lateral | Healed |
| 7 | KL | F | 14 | Peritonitis | Duod. lateral | Healed |
| 8 | HM | F | 34 | Exploded intest. | Gastric | Healed |
| 9 | VC | F | 73 | Duodenal Ulcer | Duod. lateral | Healed |
| 10 | OM | M | 66 | Stomach Ulcer | Esophagus | Healed |
| 11 | MP | F | 56 | Eventration | Yeyun. | Deceased |
| 12 | GI | F | 38 | Colicestomic | Duod. lateral | Healed |
| 13 | DA | F | 75 | Colon Ulcer | Gastric | Healed |
| 14 | CC | M | 55 | Bullet wound | Terminal | Healed |

**MP passed away due to pulmonary infection acquired prior to the fistula wound

The above Table 1 shows the lack of infections due to the treatment with this instant invention.

Figure 9:
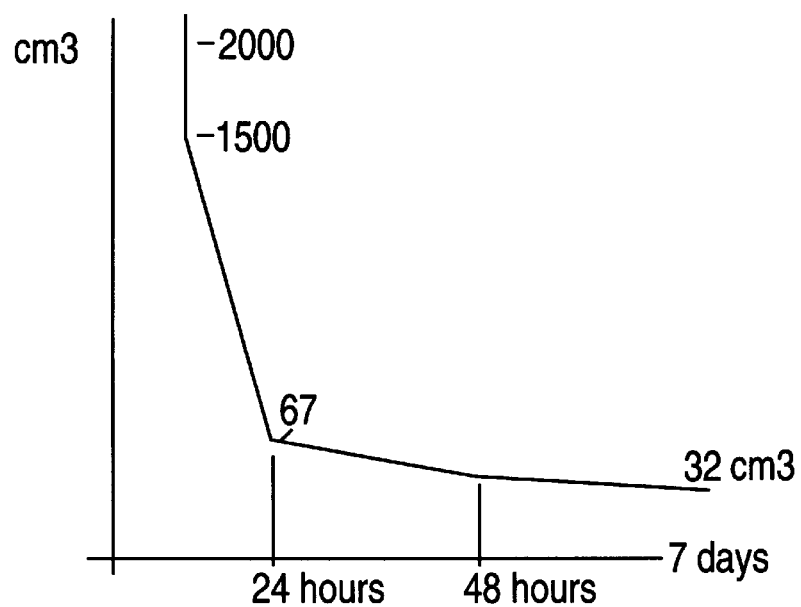
FIG. 9 illustrates the graphs of the reduction in the flow rate of the intestinal liquids in time, before this instant invention has been applied to the fistula, and after its application.

The following Table 3, interpreted in conduction with FIG. 9, relates the time needed for the patient to walk, and the correlative patient's increase in weight due to a better and correct food assimilation and the lack of loss of nutrient liquids through the fistula.

TABLE 2

Initial time of oral feeding + patient's ambulation with elimination of intravenous feeding in batch of patients treated with this instant invention, compared with another batch of patients under traditional treatment

| Patient | time prior to treatment with this invention | Time of application of this invention | | |
|---|---|---|---|---|
| | | oral feeding | walking | without VVC |
| 1 | 18 days | 1 day | 2 days | 2 days |
| 2 | 15 days | 1 day | 2 days | 2 days |
| 3 | 28 days | 2 days | 2 days | 4 days |
| 4 | 45 days | 1 day | 2 days | 5 days |
| 5 | 35 days | 1 day | 3 days | 5 days |
| 6 | 30 days | 1 day | 3 days | 5 days |
| 7 | 27 days | 7 days | 30 days | |
| 8 | 43 days | 9 days | 10 days | 20 days |
| 9 | 28 days | 3 days | 5 days | 8 days |
| 10 | 40 days | 4 days | 10 days | 10 days |
| 11 | 130 days | | | |
| 12 | 37 days | 3 days | 10 days | 7 days |

TABLE 2-continued

Initial time of oral feeding + patient's ambulation with elimination of intravenous feeding in batch of patients treated with this instant invention, compared with another batch of patients under traditional treatment

| Patient | time prior to treatment with this invention | Time of application of this invention | | |
|---|---|---|---|---|
| | | oral feeding | walking | without VVC |
| 13 | 35 days | 7 days | 10 days | 20 days |
| 14 | 31 days | 6 days | 7 days | 14 days |

VVC = feeding by means of a needle placed into an artery

It is observed in the graphic at FIG. 9 the correlation between the stoppage of the fluid's outlet with the remarkable recovery of the patient, and these results could not be reached with any of the healing methods of the prior art.

As the healing is progressing, always maintaining the negative pressure over the chamber formed by the plastic film and the flax therein placed, the wound starts to heal due to the absence of infections and because said wound is kept dry, the orifice starts to close and it expels the foreign body which is said flax.

To help the patient to start moving, it is foreseen the use of portable vacuum units, because said vacuum compacting the flax cannot be eliminated nor dispensed with as long as the treatment is not completed.

Figure 8:
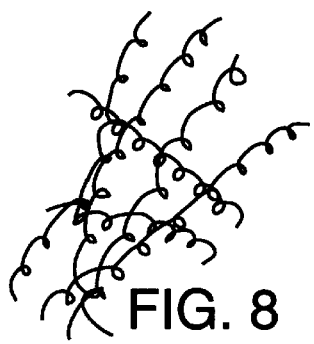
FIG. 8 illustrates a very enlarged detail of a bundle of flock.

FIG. 8 shows a simplified flax filaments used in this instant invention.

It is interesting to notice the adherence caused between said flax and the surrounding tissue due to the multiple micro-anchoring of the points of filaments into said tissue when the sudden depression is provided. It is also possible after some time, to disconnect the vacuum source withdrawing the tube through the film, sealing the orifice.

What is claimed is:

1. A healing device applied to wounds, fistulas, pancreatitis, varicose ulcers, and other medical or veterinary pathologies of a patient requiring compacting into said wound an aerated material by means of atmospheric depression, comprising a compacting chamber for covering the wound over the affected or diseased zone of the patient, said compacting chamber including a self adhesive polymeric material laminar sheet, said sheet being made out of a waterproof material said compacting chamber having a replaceable mass of aerated polymer fiber flock therewithin, said mass of fiber flock comprising a wound-stabilizing dressing;

said compacting chamber having vacuum means for deforming said compacting chamber and compacting said mass of polymer fiber flock into effective healing contact with the wound;

said vacuum means being user controllable; said vacuum being terminated upon achieving compaction of said mass of polymer fiber flock and effective healing contact of said mass of polymer fiber flock with the wound; and further wherein said laminar sheet of said compacting chamber being a low deformation, two-axis oriented polymer laminate sheet, which said polymer laminate sheet adheres over at least a perimetral portion around the zone of the patient affected with the pathology to be treated; under said laminar sheet and in intimate contact with said pathology there being placed said mass of polymer flock, said polymer fiber flock being made out of fibers with a diameter ranging from 0.0005 mm to 1 mm, and a length ranging from 3 cm. up to 50 cm, said laminar sheet being perforated by inner end of an aspiration tubes said aspiration tube being introduced into said mass of fibers for establishing an airtight relationship between said aspiration tube and said laminar sheet at said perforation;

an outer end of said aspiration tube being connected to a flow valve having a turn therein, which said flow valve at its said turn connects to upper end of a vessel;

said vessel being hermetically sealed, and from a lower end thereof said vessel having a second flow valve, said second flow valve being normally closed, said second flow valve being a selective draining means for said vessel;

said vessel being a collector for liquids, secretions, detritus and air from said area with said pathology, and from said vessel there being provided a vacuum meter calibrated between a maximum and minimum pressure, said vacuum meter cooperating between said two maximum and minimum pressure values with a shut-off valve in a conduit connecting said vessel with said vacuum pump, said vacuum meter determining a predetermined appropriate compactness of said polymeric flock, reducing a predetermined volume of said polymeric flock and driving in free ends thereof against the walls of the patient's afflicted zone, thereby providing a multiple anchoring of said polymeric flock, and said mass of flock having a variable and adjustable amount of air enclosed therein, said mass of flock having a rigidity being in a direct function of said vacuum thus established in said chamber.

2. The healing device applied to wounds, according to claim 1, wherein said vessel is hermetically separated in two volumes vertically placed one on top of each other and said volumes of said vessel being interconnected through a flow valve which is selectively open, and said vessel having at said lower volume a second flow valve communicating with an outer ambient environment through a draining hole.

3. The healing device applied to wounds, according to claim 1 or 2, wherein said vessel has a volume ranging from 5 to 30 liters capacity, and the vacuum pump is able to reduce the pressure up to −700 Hg/mm, with an extraction flow rate of 100 to 300 liters/ minute.

4. The healing device applied to wounds, according to claim 1, wherein said pathology to be healed is a wound within which it is placed the flock, and the wound is then covered by said waterproof laminar sheet, perimetrically adhered to said zone.

5. The healing device applied to wounds, according to claim 1, wherein said pathology to be healed is a bone fracture and the flock is a blanket placed around the limb with said fracture, being the fractured zone annularly surrounded by said waterproof laminar sheet, adhered against the skin in two distal stripes within which said flock blanket is contained.

6. A method to apply said healing device according to claim 1, comprising the following sequence of steps:

placing, over the zone of the patient afflicted with the pathology and in all the volume of the wound thus delimited, a mass of polymeric flock, preferably of crimped fibers with a diameter from 0.0005 mm to 1 mm, and with a length in between 3 cms up to 50 cms, forming said fibers into a bundle or a non-woven of flock, or a web with a web value of 0.5 to 6 deniers, forming an obturation plug in said fistula or a rigid layer against the bone fracture, and substantially at a level with the skin of the patient;

then placing over the zone with the pathology to be treated, and covering entirely same, with a self adhesive polymeric material laminar sheet, made out of a low deformability, waterproof, two-axis oriented polyolefinic polymer, said polymeric material laminar sheet having a thickness between 10 to 30 microns, said laminar sheet being adhered against the skin of the patient by means of a known adhesive; creating a compacting airtight chamber over said area with the pathology to be treated, covering the skin of the patient over said area and covering said mass of flock as well, said laminar sheet being self-adhesive;

said laminar sheet being perforated by an end of an aspiration tube being introduced into said mass of fibers, establishing an airtight relationship between said tube and said laminar sheet at said perforation;

closing said first flow valve and producing a vacuum by activating a vacuum pump extracting the air contained within said chamber, sending said extracted air into said vessel, maintaining an activity of said vacuum pump until a negative pressure of around 700 mm/Hg is attained, and with an air extraction flow rate of 100 to 300 liters/ minute; once a predetermined programmed depression is attained, said vacuum pump is detained, either cutting of its power source or acting over the second flow valve or a shut-off valve;

keeping a stabilized depression in said vessel, said first flow valve being opened, producing an instant compactness of said mass of fibers;

maintaining a stabilized depression at reasonable constant values between said compacting chamber and said vessel, with the vacuum pump shut off, while said compactness of the mass of fibers is maintained at a value between 80 to 95% of the original value, forming a compacted mass due to the action of said vacuum, and a positive pressure over the abdominal walls compensating the pressures within the body of the patient;

at the necessary intervals of time, closing said first flow valve, keeping the values of said vacuum in said airtight chamber, and opening said second flow valve producing draining of said contents of said vessel, then closing said second flow valve and opening one more time again said first flow valve;

repeating said operations for the necessary time required until the healing process has been completed.

7. The healing device applied to wounds as in claim 1 wherein said fibers of said mass of polymer fiber flock are chosen from crimped fibers, each said crimped fiber being placed with its respective axis being substantially parallel to each other axis.

8. The healing device applied to wounds as in claim 1 wherein said fibers of said mass of polymer fiber flock are chosen from a non-woven mass of flock.

9. The healing device applied to wounds as in claim 1 wherein said fibers of said mass of polymer fiber flock are chosen from a fabric of a web made out of said fibers, said web measuring from 0.5 to 6 deniers.

* * * * *